United States Patent [19]

Ailloud et al.

[11] 4,216,063
[45] Aug. 5, 1980

[54] PROCESS FOR RECOVERY OF TOLUENE DIISOCYANATE

[75] Inventors: Pierre Ailloud, Marcq eb Baroeul; Philippe D'Haussy, Saint Andre, both of France

[73] Assignee: Produits Chimiques Ugine Kuhlmann, Paris, France

[21] Appl. No.: 918,581

[22] Filed: Jun. 23, 1978

[30] Foreign Application Priority Data

Jul. 12, 1977 [FR] France .................................. 77 21436

[51] Int. Cl.² ............................................. B01D 1/24
[52] U.S. Cl. ..................................... 203/91; 159/6 W; 159/DIG. 10; 260/453 SP
[58] Field of Search ..................... 203/91, 6; 159/6 W, 159/6 WH, DIG. 10; 260/453 SP

[56] References Cited

U.S. PATENT DOCUMENTS

| | | | |
|---|---|---|---|
| 2,706,169 | 4/1955 | Beck | 260/453 SP X |
| 2,974,725 | 3/1961 | Samesreuther et al. | 159/6 W |
| 3,457,291 | 7/1969 | Baylor | 203/91 X |
| 3,542,112 | 11/1970 | Monty | 159/6 WH |

FOREIGN PATENT DOCUMENTS 2320938  3/1977  France .................................. 260/453 SP

OTHER PUBLICATIONS

Kontro Co., "Thin-Film Evaporator Can Produce Dry Powders"; Chemical Engineering; Dec. 23, 1963; pp. 52–53.

*Primary Examiner*—Arnold Turk
*Attorney, Agent, or Firm*—Pennie & Edmonds

[57] ABSTRACT

A process for the continuous and automatic separation of toluene diisocyanate, without decomposition, from distillation residues comprising evaporating toluene diisocyanate in an agitated, scraped evaporator, under a vacuum of about 1 mm Hg to about 50 mm Hg and at a temperature of about 210° C. to about 250° C., with a minimum residence time, preferably about 15 minutes, in an evaporator, and continuously extracting the remaining components of the residue.

7 Claims, No Drawings

PROCESS FOR RECOVERY OF TOLUENE DIISOCYANATE

FIELD OF THE INVENTION

The present invention relates to a process of separation of toluene diisocyanate (TDI) from crude mixtures of reaction masses such as heavy, viscous distillation bottoms.

BACKGROUND OF THE INVENTION

During conventional manufacture of TDI, 10 to 15% by weight of a viscous liquid mixture residue is formed. This mixture can be concentrated by distillation so that it contains 30 to 40% by weight TDI and 60 to 70% by weight of other components. Because the viscosity of the mixture is increased during distillation, it is difficult to further distill the mixture to obtain higher component concentrations to facilitate TDI recovery. Consequently, it is necessary to develop different techniques to recover TDI from such residue mixtures and collect residual components in the form of combustible components no longer containing TDI and to avoid both pollution by toxic vapors and loss of TDI.

Various techniques have been proposed to recover TDI from the residues, for example, that described in U.S. Pat. No. 3,405,040 where the residue mixture is combined with oil at 220° C. under a pressure of 20 mm Hg. The TDI content of that mixture undergoes flash evaporation and the other components precipitate in the form of a solid which is separated from the oil by drying and then that solid is burned. Another technique described in French Pat. No. 2,091,813 teaches recovery of TDI by solvent extraction from the non-TDI component produced during distillation. However, those techniques are undesirable because they are batch processes and require costly raw materials and have high energy consumption.

Other processes try to eliminate these drawbacks by proposing the direct separation of the TDI from the other components of the mixture by evaporation of the TDI under vacuum and direct transformation of the residual components into solids. However, these processes have the drawback of being either batch operations, such as the process described in U.S. Pat. No. 3,457,291, or of being difficult to use, such as the process of French Pat. No. 2,320,938.

All such direct separation processes have the characteristic of rapid production of a thin layer of solid residues either on a hot wall of, or on a bed of hot solid residues in a separation apparatus to avoid risk of polymerization of the TDI and other components at separation temperatures and residence times and of the release of carbon dioxide or other gases from decomposition of the TDI, which decomposition risks formation of foams in the mass to be separated.

DETAILED DESCRIPTION OF THE PREFERRED EMBODIMENTS

Applicants have developed a continuous process of separation of TDI from distillation residues, and of extraction of these residues in solid form. This process offers the advantage of being simple, easy and reliable to use, avoiding formation of foam or decomposition products. Residues from applicants' process do not contain more than slight TDI concentrations.

Separation takes place in an agitated and scraped type evaporator such as that described in French Pat. No. 2,039,628. Separation pressure, temperature and residence time are selected to avoid decomposition of TDI into gas, polymers or various byproducts, and to avoid formation of foam, which would preclude use of such apparatus.

It has been shown that starting from about 220° C. to about 250° C., TDI quickly decomposes into $CO_2$ and other gases and that formation of such gas in the viscous mixture causes foam. However, the mixture should be hot enough for TDI to be evacuated.

Applicants have solved this problem by continuously heating the residue mixture on a wall at a maximum temperature of 250° C., evaporating the TDI at a rather low temperature from about 70° C. to about 175° C. and preferably from about 100° C. to about 130° C., under a pressure of about 1 to 50 mm Hg and preferably about 5 to about 20 mm Hg, with agitation of the mixture to promote mass transfer. This mixture is progressively moved along the wall of the evaporator to a temperature of about 210° C. to about 250° C., and preferably from about 220° C. to about 230° C., where the mixture transforms from the viscous liquid state to a paste state and then to a solid state. Agitation should be sufficient to assure heat exchange, progression of the products in the evaporator, scraping of the solids and breaking of any foams formed. The capacity of the evaporator should be such that it allows a sufficient residence time (from about 15 to about 45 minutes) to assure the transformation of materials.

The exiting solids contain less than 3% by weight TDI. Their temperature can then be brought, without risk of foaming, to a higher temperature (about 280° C.) before exiting the apparatus to evacuate the last traces of TDI. The porous, fragmented, dry solids are collected under vacuum in a collection means operating as a sieve or better still are continuously extruded under vacuum with a hot screw through a spinneret. Solid residues in the form of powder or compact granules are picked up by a pneumatic transport means and directed toward an incinerator, while the TDI is condensed in a conventional manner.

The process of the subject invention offers the advantages of being able to operate continuously and entirely automatically and avoids pollution. Further, the subject invention requires little heat or mechanical energy and is therefore very economical.

An apparatus having a dimension of about 20 to 25 m$^2$ and a volume of about 1600 liters, followed by an extruder, is sufficient to assure the continuous separation of residue and TDI and to assure TDI production of 30,000 tons/year.

The following examples illustrate the invention without, however, limiting it:

EXAMPLE I

A mixture made up of 43% TDI and 57% heavy compounds coming from the bottom of a concentration column is introduced into an evaporation apparatus at a rate of 60 kg/h m$^2$. The apparatus has a heated surface area of 0.86 m$^2$ and a total volume of 20 liters and has two self-cleaning agitation screws turning at different speeds. Under a pressure of 12 mm Hg, the mixture is progressively brought to a temperature of 215° C., and is transformed into a powder containing 2.8% TDI after a residence time of 15 minutes in the apparatus.

TDI is condensed and collected, and solid residues are extruded under vacuum through a spinneret in the form of granules 6 mm in diameter and 15 mm long, at a feed rate of 30 kg/h.

EXAMPLES II to IV

Operating as in Example I, but with different feed rates and residence times, the following results are obtained:

| Feed Rate (kg/h m$^2$) | Residence Time (minutes) | Final TDI Concentration (% of weight of residue) |
| --- | --- | --- |
| 50 | 18 | 1.5 |
| 70 | 13 | 3.4 |
| 25 | 36 | 0.05 |

Example II shows that a minimum residence time, such as that in Example I, is required, preferably 15 minutes, if a minimum TDI concentration in the residues is desired.

It is not intended to limit the present invention to the specific embodiments described above. Other changes may be made in the process and apparatus specifically described herein without departing from the scope and teachings of the instant invention, and it is intended to encompass all other embodiments, alternatives and modifications consistant with the present invention.

We claim:

1. A process for the continuous separation of toluene diisocyanate, without decomposition thereof, from a crude residue mixture of reaction mass containing the toluene diisocyanate which comprises:
    (a) continuously introducing the residue mixture into an agitated, scraped evaporator under a pressure of 1 to 50 mm Hg for a minimum residence time of 15 minutes;
    (b) evaporating the toluene diisocyanate at an initial temperature between about 70° C. to about 175° C.;
    (c) moving the residue mixture progressively along the wall of the evaporator to a temperature of about 210° C. to about 250° C.;
    (d) condensing and collecting the evaporated toluene diisocyanate; and
    (e) collecting the dry solid residue under vacuum.

2. The process according to claim 1 wherein the pressure is selected in the range from about 5 to about 20 mm Hg.

3. The process according to claim 1 wherein the initial temperature is selected in the range from about 100° C. to about 130° C.

4. The process according to claim 1 wherein the increased temperature is selected in the range from about 220° C. to about 230° C.

5. The process according to claim 1 wherein the dry solid residue is collected by extrusion under vacuum with an extrusion means.

6. The process according to claim 1 wherein the dry solid residue is collected under vacuum by a sieve collection means.

7. The process according to claim 1 wherein the concentration of toluene diisocyanate in the collected dry solid residue is less than 3% by weight.

* * * * *